United States Patent
Hamann et al.

(10) Patent No.: US 9,002,457 B2
(45) Date of Patent: Apr. 7, 2015

(54) IMPLANTABLE MEDICAL DEVICE WITH CONTROL OF NEURAL STIMULATION BASED ON BATTERY STATUS

(71) Applicant: Cardiac Pacemakers, Inc., St. Paul, MN (US)

(72) Inventors: Jason J. Hamann, Blaine, MN (US); Scott Vanderlinde, Plymouth, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/948,790

(22) Filed: Jul. 23, 2013

(65) Prior Publication Data

US 2014/0058467 A1 Feb. 27, 2014

Related U.S. Application Data

(60) Provisional application No. 61/692,060, filed on Aug. 22, 2012.

(51) Int. Cl.

| | |
|---|---|
| *A61N 1/36* | (2006.01) |
| *A61N 1/378* | (2006.01) |
| *A61N 1/37* | (2006.01) |
| *A61B 5/00* | (2006.01) |
| *H01M 10/48* | (2006.01) |
| *H02J 7/00* | (2006.01) |
| *G01R 31/36* | (2006.01) |

(52) U.S. Cl.
CPC ............. *A61N 1/3787* (2013.01); *A61N 1/378* (2013.01); *A61N 1/3605* (2013.01); *A61N 1/3708* (2013.01); *A61B 5/0006* (2013.01); *A61N 1/36053* (2013.01); *H01M 10/48* (2013.01); *A61B 2560/0204* (2013.01); *H02J 2007/005* (2013.01); *G01R 31/3606* (2013.01); *H02J 7/0047* (2013.01); *H02J 7/0063* (2013.01); *H02J 2007/0067* (2013.01)

(58) Field of Classification Search
CPC ... A61N 1/3708; A61N 1/378; A61N 1/3787; A61N 1/37; A61N 1/3605; A61N 1/36053; A61N 1/36125; A61N 1/36128
USPC ...................................................... 607/44–45
See application file for complete search history.

(56) References Cited

U.S. PATENT DOCUMENTS

| | | | |
|---|---|---|---|
| 7,065,412 B2 | 6/2006 | Swoyer et al. | |
| 7,142,923 B2 | 11/2006 | North et al. | |
| 7,194,308 B2 | 3/2007 | Krig et al. | |
| 7,941,220 B2 | 5/2011 | Tobacman | |
| 2009/0018607 A1* | 1/2009 | Crowley et al. | 607/44 |

* cited by examiner

*Primary Examiner* — Rex R Holmes
(74) *Attorney, Agent, or Firm* — Schwegman Lundberg & Woessner, P.A.

(57) ABSTRACT

An implantable medical device is powered by a battery to deliver one or more therapies including at least one non-life-sustaining therapy such as neural stimulation for enhancing quality of life of a patient. When the battery approaches its end of life, the implantable medical device reduces power consumption of the neural stimulation (e.g., intensity of the neural stimulation) for extending the remaining battery life while maintaining a certain amount of therapeutic benefits for the patient. In one embodiment, the intensity of the neural stimulation is reduced in a tiered manner. In one embodiment in which the implantable medical device also delivers at least one life-sustaining cardiac stimulation therapy, the neural stimulation is disabled or adjusted to reduce its power consumption (e.g., intensity) while the intensity of the cardiac stimulation therapy is maintained when the battery is near its end of life.

20 Claims, 9 Drawing Sheets

IMPLANTABLE MEDICAL DEVICE WITH CONTROL OF NEURAL STIMULATION BASED ON BATTERY STATUS

CLAIM OF PRIORITY

This application claims the benefit of priority under 35 U.S.C. §119(e) of U.S. Provisional Patent Application Ser. No. 61/692,060, filed on Aug. 22, 2012, 2010, which is herein incorporated by reference in its entirety.

TECHNICAL FIELD

This document relates generally to implantable medical devices and more particularly to an implantable medical device providing for at least neural stimulation and control of device functions including the neural stimulation based on battery status.

BACKGROUND

Neural stimulation has been applied to modulate various physiologic functions and treat various diseases. One example is the modulation of cardiac functions using autonomic modulation therapy (AMT) such as vagus nerve stimulation (VNS) therapy in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of VNS is utilized, for example, to control myocardial remodeling.

Batteries are used as energy sources for implantable medical devices including those delivering neural stimulation. While the use of a battery allows a medical device to be totally implantable, without the need of transcutaneous power transmission, the power consumption and longevity of the medical device is limited by the capacity of the battery. For example, many implantable medical devices providing for cardiac and/or neural stimulation treating cardiac disorders are long-term treatments that may last up to the patient's lifetime. When the battery of such an implantable medical device is no longer able to provide sufficient energy for the operation of the device, the device is to be explanted and replaced. Because it may take weeks to months to arrange for the device replacement after such need is indicated based on the energy state of the battery, there is a need to manage behavior of the implantable medical device during this period of time, when the battery is near its end of life.

SUMMARY

An implantable medical device is powered by a battery to deliver one or more therapies including at least one non-life-sustaining therapy such as neural stimulation for enhancing quality of life of a patient. When the battery approaches its end of life, the implantable medical device reduces power consumption of the neural stimulation (e.g., intensity of the neural stimulation) for extending the remaining battery life while maintaining a certain amount of therapeutic benefits for the patient. In one embodiment, the intensity of the neural stimulation is reduced in a tiered manner. In one embodiment in which the implantable medical device also delivers at least one life-sustaining cardiac stimulation therapy, the neural stimulation is disabled or adjusted to reduce its power consumption (e.g., intensity) while the intensity of the cardiac stimulation therapy is maintained when the battery is near its end of life.

In one embodiment, an implantable medical device can include a battery, a battery monitoring circuit, a neural stimulation circuit, and a control circuit. The battery monitoring circuit is configured to monitor an energy level of the battery and produce a battery status parameter indicative of the energy level. The neural stimulation circuit is configured to deliver neural stimulation for modulating neural activities. The control circuit can include a power controller and a neural stimulation controller. The power controller can be configured to set a current power mode of the implantable medical device to a reduced-power operation mode of a plurality of power modes in response to the battery status parameter indicating that the energy level has fallen below an energy level threshold of a plurality of energy level thresholds. The neural stimulation controller is configured to control the delivery of the neural stimulation using neural stimulation parameters and can be configured to adjust one or more parameters of the neural stimulation parameters within the reduced-power operation mode such that a power consumption of the neural stimulation is reduced within the reduced-power operation mode according to a specified power reduction schedule.

In one embodiment, a method for operating an implantable medical device is provided. An energy level of a battery of the implantable medical device is monitored. A battery status parameter indicative of the energy level is produced. Neural stimulation is delivered for modulating neural activities. The delivery of the neural stimulation is controlled using neural stimulation parameters. A current power mode of the implantable medical device can be set to a reduced-power operation mode of a plurality of power modes in response to the battery status parameter indicating that the energy level has fallen below an energy level threshold of a plurality of energy level thresholds. A power consumption of the neural stimulation can be reduced within the reduced-power operation mode by adjusting one or more parameters of the neural stimulation parameters according to a specified power reduction schedule.

In one embodiment, an implantable medical device includes a battery, a battery monitoring circuit, a plurality of functional modules, and a control circuit. The battery monitoring circuit is configured to monitor an energy level of the battery and produce a battery status parameter indicative of the energy level. The plurality of functional modules can include a neural stimulation module and a cardiac stimulation module. The neural stimulation module includes a neural stimulation circuit configured to deliver neural stimulation for modulating neural activities in the nervous system of a body. The cardiac stimulation module includes a cardiac stimulation circuit configured to deliver one or more of pacing or defibrillation pulses to the heart of the body. The control circuit can be configured to control operation of each functional module of the one or more functional modules and to reduce a power consumption of the neural stimulation in response to the battery status parameter indicating that the energy level has fallen below an energy level threshold of a plurality of energy level thresholds.

In one embodiment, a method for operating an implantable medical device in a body is provided. An energy level of a battery of the implantable medical device is monitored. A battery status parameter indicative of the energy level is produced. Delivery of neural stimulation for modulating neural activities in the nervous system from the implantable medical device and delivery of cardiac stimulation including one or more of pacing or defibrillation pulses to the heart from the implantable medical device can be controlled. Such control can include reducing a power consumption of the neural stimulation in response to the battery status parameter indicating that the energy level has fallen below an energy level threshold of a plurality of energy level thresholds.

An example of reducing the power consumption of the neural stimulation includes reducing the intensity of the neural stimulation. Another example of reducing the power consumption of the neural stimulation includes suspending delivery of the neural stimulation when a temporary power-consumptive event is occurring, such as when the implantable medical device is transmitting and/or receiving signals via telemetry.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
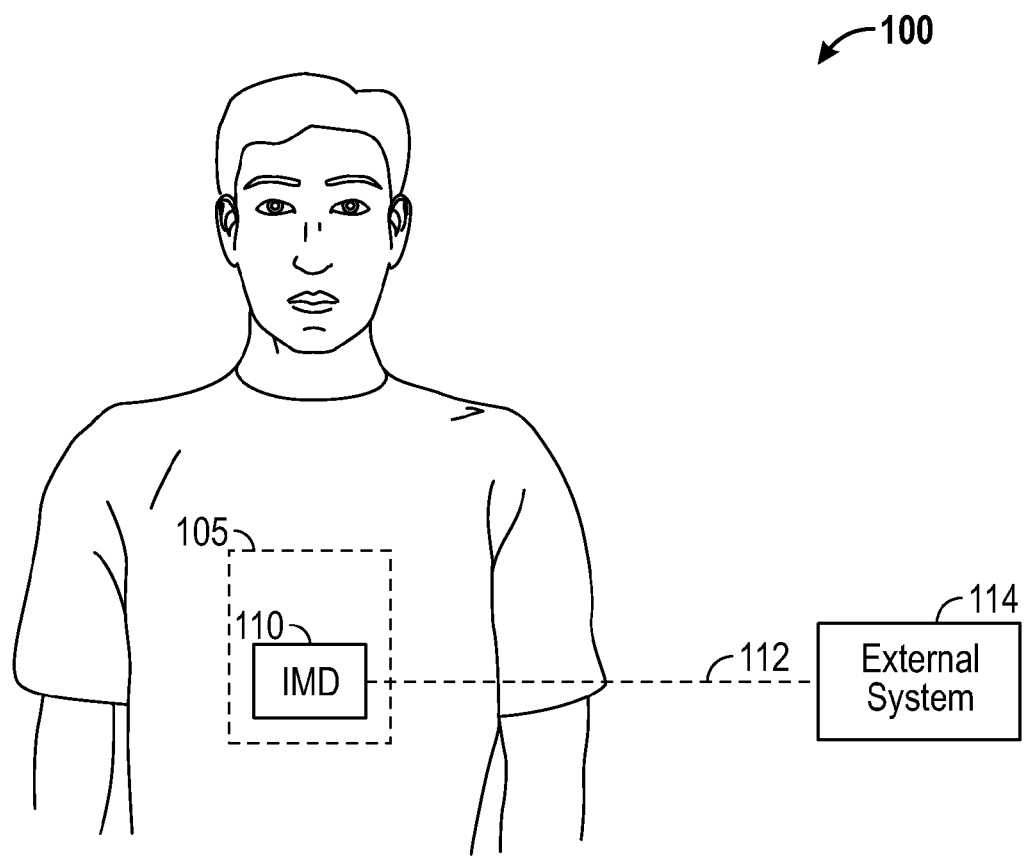
FIG. 1 is an illustration of an embodiment of an implantable medical device (IMD) system and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for controlling operation of an implantable medical device (IMD) based on the energy level of its battery (non-rechargeable or rechargeable battery). In various embodiments, the IMD delivers at least one non-life-sustaining therapy, such as an autonomic modulation therapy (AMT) delivered to a patient to enhance the patient's quality of life. When the energy level indicates that the battery is approaching its end of life, the power consumption of the non-life-sustaining therapy is reduced to extend the remaining life of the battery while maintaining a certain level of therapeutic benefits received by the patient. In various embodiments, in addition to the non-life-sustaining therapy, the IMD delivers at least one life-sustaining therapy such as a bradycardia therapy for a pacemaker-dependent patient or a ventricular defibrillation therapy. When the energy level indicates that the battery is approaching its end of life, the intensity of the life-sustaining therapy is maintained while the non-life-sustaining therapy is disabled or delivered at a reduced power consumption.

In this document, neural stimulation includes stimulation targeted at modulating neural activities, including stimulation that is applied to one or more nerves or natural sensors such as baroreceptors, and cardiac stimulation includes stimulation targeted at modulating cardiac rhythms, including pacing and defibrillation pulses that are delivered to the heart directly or through other body tissue. While neural stimulation and cardiac stimulation are discussed as examples of non-life-sustaining therapy and life-sustaining therapy in this document, respectively, the present subject matter applies to an IMD delivering any one or more non-life-sustaining therapies or an IMD delivering both non-life-sustaining and life-sustaining therapies. The present method and system can be applied to provide sufficient power for each life-sustaining therapy while reducing the amount of power consumed by each non-life-sustaining therapy as the battery of the IMD approaches its end of life. While IMDs are discussed as examples, the present method and system can be applied to any battery-powered medical devices.

FIG. 1 is an illustration of an embodiment of an IMD system 100 and portions of an environment in which system 100 used. System 100 includes an implantable system 105, an external system 114, and a telemetry link 112. Implantable system 105 includes an IMD 110 and is placed in a patient as illustrated in FIG. 1. External system 114 and IMD 110 communicates via telemetry link 112.

IMD 110 is powered by a battery, such as a primary cell battery or a rechargeable battery. In various embodiments, IMD 110 is a neural sensing and/or stimulation device. One example of such a device includes an AMT device that delivers neural stimulation to the autonomic nervous system, such as a vagus nerve. The neural sensing and/or stimulation functions are adjustable based on the status of the battery. For example, when the energy level of the battery falls below a specified threshold, the intensity of a non-life-sustaining neural stimulation therapy is reduced or stopped, or other power consuming features of IMD 110 (e.g. sensing not required by a life-sustaining therapy, telemetry, etc.) may be adjusted or shut off to reduce power consumption, to extend the remaining battery life. In various embodiments, IMD 110 integrates a cardiac rhythm management (CRM) device with a neural sensing and/or stimulation device. The CRM device senses cardiac electrical activities and/or delivers cardiac stimulation. Examples of the CRM device include pacemakers, cardioverter/defibrillators, combined pacemaker-cardioverter/defibrillators, cardiac resynchronization therapy (CRT) devices, and cardiac remodeling control therapy (RCT) devices. In various embodiments, cardiac activities are sensed to indicate a need for cardiac stimulation and/or to control the timing of pacing pulse deliveries. In various embodiments, cardiac activities are sensed to control the timing of neural stimulation pulse deliveries, such as to synchronize neural stimulation to cardiac cycles. The neural sensing and/or stimulation functions and the cardiac sensing and/or stimulation functions can be adjustable based on the status of the battery. For example, when the energy level of the battery falls below a specified threshold, the intensity of a non-life-sustaining neural stimulation therapy is reduced or stopped for extending the remaining battery life, while the intensity of a life-sustaining cardiac stimulation therapy remains unadjusted for ensuring patient safety. Examples of the life-sustaining cardiac stimulation therapy include ventricular defibrillation therapy and bradycardia pacing therapy for pacemaker-dependent patients.

External system 114 receives and processes data transmitted from IMD 110 and controls operation of IMD 110. In one embodiment, external system 114 includes a programmer that allows a user such as a physician or other caregiver to monitor the patient wearing IMD 110 and program IMD 110 through telemetry link 112. In another embodiment, external system 114 includes a patient monitoring system that includes an external device communicating with IMD 110 through telemetry link 112 and a remote device coupled to the external device via a telecommunication network to allow the user to monitor the patient and/or program IMD 110 from a remote location.

Telemetry link 112 provides for communication between IMD 110 and external system 114. In one embodiment, telemetry link 112 is an inductive telemetry link. In an alternative embodiment, telemetry link 112 is a far-field radio-frequency telemetry link. In one embodiment, telemetry link 112 includes both an inductive telemetry link and a far-field radio-frequency telemetry link. In other words, IMD 110 and external system 114 are configured to communicate with each other using inductive and/or far-field radio-frequency telemetry. The communication includes data transmission from IMD 110 to external system 114, including, for example, transmitting the data representative of sensed cardiac, neural, and/or other physiological signals in real time, extracting the data representative of sensed cardiac, neural, and/or other physiological signals stored in IMD 110, and extracting data indicating an operational status of IMD 110 (e.g., battery status). The communication also includes data transmission from external system 114 to IMD 110, including, for example, programming IMD 110 to produce the data representative of the sensed cardiac, neural, and/or other physiological signals, programming IMD 110 to perform at least one self-diagnostic test (such as for a device operational status), programming IMD 110 to deliver cardiac and/or neural stimulation therapies, and programming IMD 110 for adjusting its operations based on the status of the battery.

Figure 2:
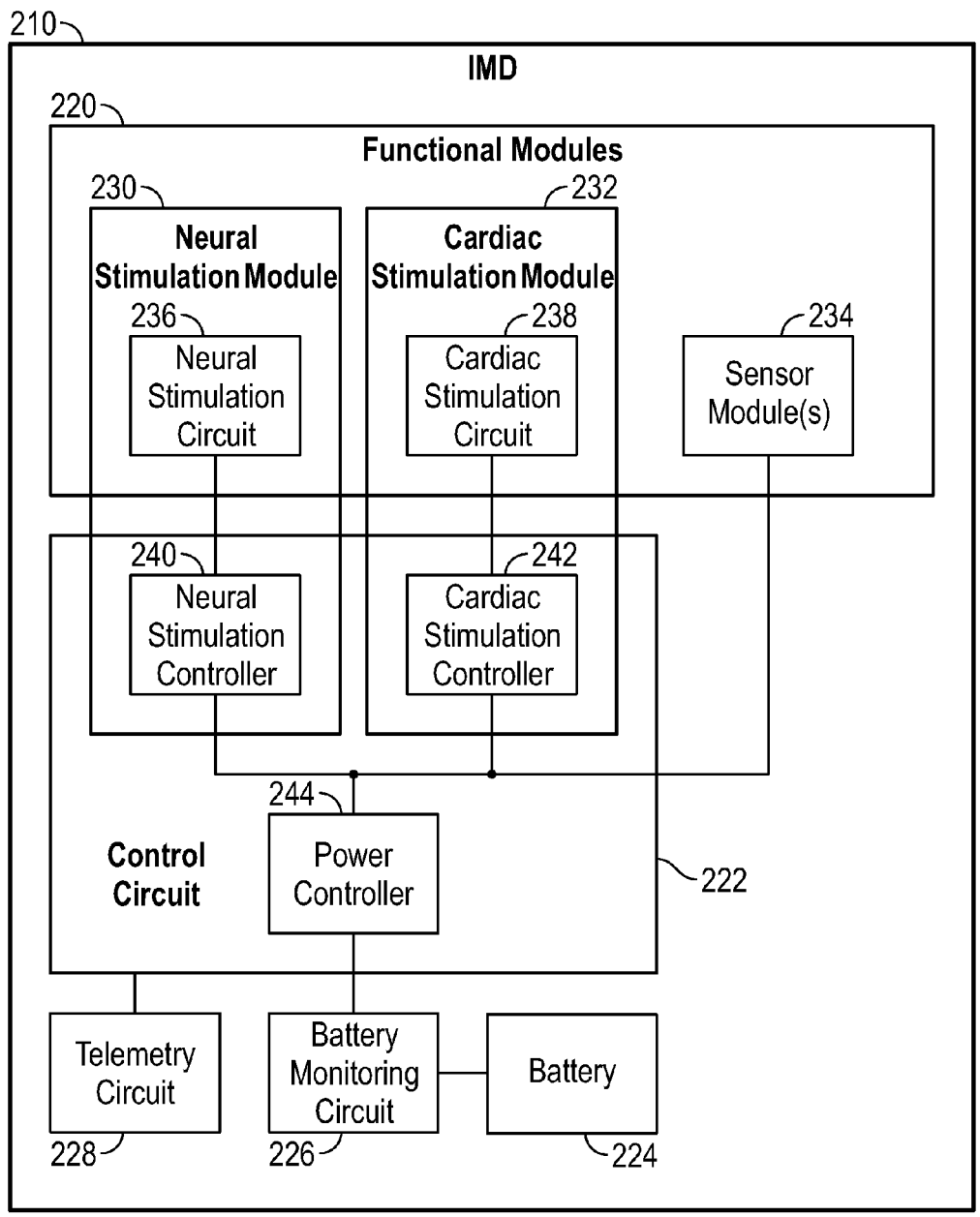
FIG. 2 is a block diagram illustrating an embodiment of an IMD.

FIG. 2 is a block diagram illustrating an embodiment of an IMD 210, which represents an embodiment of IMD 110. IMD 210 includes a battery 224, a battery monitoring circuit 226, a plurality of functional modules 220, a telemetry circuit 228, and a control circuit 222.

Battery monitoring circuit 226 monitors battery 224 and produces a battery status parameter indicative of the energy level or state of depletion of battery 224. Examples of battery 224 include a primary cell battery and a rechargeable battery. In one embodiment, battery monitoring circuit 226 measures one or more battery parameters indicative of an energy level of battery 224. Examples of the one or more battery parameters include a terminal voltage, a charging time, and charge depletion parameter. The terminal voltage is the voltage across the two terminals of battery 224. The charging time is a time interval during which a capacitor in the IMD 110 (such as a defibrillation capacitor, if IMD 110 includes a defibrillator) is charged to a specified energy level using battery 224. The charge depletion parameter is indicative of a cumulative charge depleted from battery 224. An example of measuring the charge depletion parameter is discussed in U.S. Pat. No. 7,194,308, entitled "SYSTEM AND METHOD FOR MONITORING OR REPORTING BATTERY STATUS OF IMPLANTABLE MEDICAL DEVICE", assigned to Cardiac Pacemakers, Inc., which is incorporated herein by reference in its entirety.

In various embodiments, the battery status parameter can be a parameter of the measured one or more battery parameters or a function of the measured one or more battery parameters. In one embodiment, battery monitoring circuit 226 analyzes the one or more battery parameters using one or more energy level thresholds and produces the battery status parameter using an outcome of the analysis. The battery status parameter has values each indicating whether the energy level of the battery has fallen below one of the one or more energy level thresholds. The one or more energy level thresholds are specified based on a need or desire for informing the patient or a user of system 100, such as the physician or other caregiver, of a need or necessity for replacement of IMD 110. Examples of the one or more energy level thresholds include "elective replacement indication" (ERI) that indicates the need for scheduling for replacement of IMD 110, "end of life" (EOL) that indicates the need for immediate replacement of IMD 110, and "battery expired" (BEX) that indicates that all functions of IMD 110, optionally with an exception for telemetry, must be disabled as the remaining energy level of battery 224 may not provide for proper performance of any of these functions. In one embodiment, ERI and EOL are each chosen and programmed for a desired remaining life expectancy of battery 224 (and hence IMD 110), such as about 3 months from ERI to EOL, and about 3 months from EOL to BEX. In one embodiment, IMD 110 has two energy level thresholds including EOL and BEX. In another embodiment, IMD 110 has three energy level thresholds including ERI, EOL, and BEX. Other energy level threshold(s) may also be employed, as desired. In various embodiments in which battery 224 is a rechargeable battery, the energy level thresholds such as ERI, EOL, and BEX may be referenced to an energy level at which recharging is necessary, rather than an end-of-life point as in the case of a non-rechargeable primary cell battery.

Functional modules 220 are each powered by battery 224. In the illustrated embodiment, functional modules 220 include a neural stimulation module 230, a cardiac stimulation module 232, and one or more sensor modules 234. Neural stimulation module 230 includes a neural stimulation circuit 236 that delivers neural stimulation to the nervous system of the patient and a neural stimulation controller 240 that controls the delivery of the neural stimulation by executing a neural stimulation algorithm for modulating electrical activities of the nervous system. Cardiac stimulation module 232 includes a cardiac stimulation circuit 238 that delivers cardiac stimulation to the heart of the patient and a cardiac stimulation controller 242 that controls the delivery of the cardiac stimulation by executing a cardiac stimulation algorithm for modulating electrical activities of the heart. Sensor module(s) 234 each include a sensor circuit configured to sense a physiological signal. In various embodiments, one or more physiological signals sensed by one or more sensor modules 234 are each used for monitoring the patient's conditions, controlling the delivery of the neural stimulation, and/or controlling the delivery of the cardiac stimulation. Functional modules 220 are illustrated in FIG. 2 by way of example but not by way of limitation. In various embodiments, IMD 210 includes one or more functional modules such as neural stimulation module 230, cardiac stimulation module 232, one or more sensor modules 234, and any combination of two or more of the modules 230, 232, or 234. In various embodiments, operation of each functional module of functional modules 220 can be adjusted based on the status of battery 224.

Telemetry circuit 228 receives incoming signals from external system 114 and transmits outgoing signals to external system 114 via telemetry link 112. In various embodiments, telemetry circuit 228 supports inductive telemetry and/or far-filed radio-frequency telemetry. In one embodiment, operation of telemetry circuit 228 is not adjusted based on the status of battery 224 such that communication with IMD 210 can be maintained after other functions of IMD 210 must be disabled as the life of the battery expires. In another embodiment, operation of telemetry circuit 228 may be limited based on the status of battery 224, such as to allow inductive telemetry only for conserving power when the battery is near its end of life.

Control circuit 222 controls operation of each functional module of functional modules 220. In the illustrated embodiment, control circuit 222 includes a power controller 244 and portions of functional modules 220 that control operation of various monitoring and therapeutic functions of IMD 210, including neural stimulation controller 240, cardiac stimulation controller 242, and circuitry for processing one or more physiological signals sensed by sensor module(s) 234. Power controller 244 controls a power state of each functional module of functional modules 220 according to a current power mode of a plurality of power modes of IMD 210. The power modes each correspond to an energy level threshold of the one or more energy level thresholds for battery 224 and specify the power state of the each functional module. Each power state corresponds to an energy level threshold. Examples of the power states for each functional module include a "normal" state in which the functional module is enabled, a "low-power" state in which the functional module is disabled, and a "reduced-power" state in which the functional module is enabled and adjusted for reducing power consumption of the functional module. The low-power state may include an "off" or "no-power" state during which the disabled functional module is completely turned off and/or a "sleep" state during which the disabled functional module is turned off but maintained at a state allowing prompt reactivation when needed. Power controller 220 switches the current power mode to a next power mode of the plurality of power modes using the battery status parameter in response to a change in the value of the battery status parameter. In various embodiments, the battery status parameters has discrete values each indicating whether the energy level of the battery has fallen below one of the one or more energy level thresholds. Thus, the change in the value of the battery status parameter indicates that the energy level of the battery has fallen below one of the one or more energy level thresholds.

Functional modules 220 have an overall power consumption for the current power mode that is the sum of the power consumptions of all the functional modules when each functional module of functional module 220 operates according to the current power mode. The overall power consumption of the next power mode is lower than the overall power consumption of the current power mode.

In various embodiments, IMD 210 includes a normal operation mode and one or more reduced-power operation modes. The current power mode of IMD 210 is set to the normal operation mode or one of the one or more reduced-power operation modes according to the value of the battery status parameter. Examples of the power states of each functional module of functional modules 220 during each operation mode of IMD 210 include:

the normal operation mode:
  neural stimulation module 230: normal state;
  cardiac stimulation module 232: normal state;
  one or more sensor modules 234: normal state;
reduced-power operation mode 1 (ERI mode or EOL mode):
  neural stimulation module 230: reduced-power state;
  cardiac stimulation module 232: normal state;
  one or more sensor modules 234: normal state or reduced-power state
reduced-power operation mode 2 (ERI mode or EOL mode):
  neural stimulation module 230: low-power state;
  cardiac stimulation module 232: normal state;
  one or more sensor modules 234: reduced-power state or low-power state;
reduced-power operation mode 3 (ERI mode or EOL mode):
  neural stimulation module 230: low-power state;
  cardiac stimulation module 232: reduced-power state;
  one or more sensor modules 234: low-power state;
reduced-power operation mode 4 (BEX mode):
  neural stimulation module 230: low-power state;
  cardiac stimulation module 232: low-power state;
  one or more sensor modules 234: low-power state.

Power controller 244 sets the power state of each functional module of functional modules 220 according to such operation modes of IMD 210. The examples above are presented for illustrative purposes only. In various embodiments, after the energy level of battery has fallen below an energy level threshold (such as ERI or EOL), indicating that the battery is approaching its end of life, a functional module performing only life-sustaining function(s) is set to the normal state, while a functional module performing only non-life-sustaining function(s) is set to the reduced-power state or low-power state. Whether, when, and which power state a non-life-sustaining functional module is set to is determined by the therapeutic benefits and risk of losing power needed for the life-sustaining function(s).

In various embodiments, the circuit of IMD 210, including its various embodiments and elements discussed in this document, can be implemented using a combination of hardware and software (including firmware). In various embodiments, control circuit 222 and battery monitoring circuit 226, including its various embodiments and elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. In various embodiments, control circuit 222 and battery monitoring circuit 226, including its various embodiments and elements discussed in this document, can be programmed to perform the various methods discussed in this document.

Figure 3:
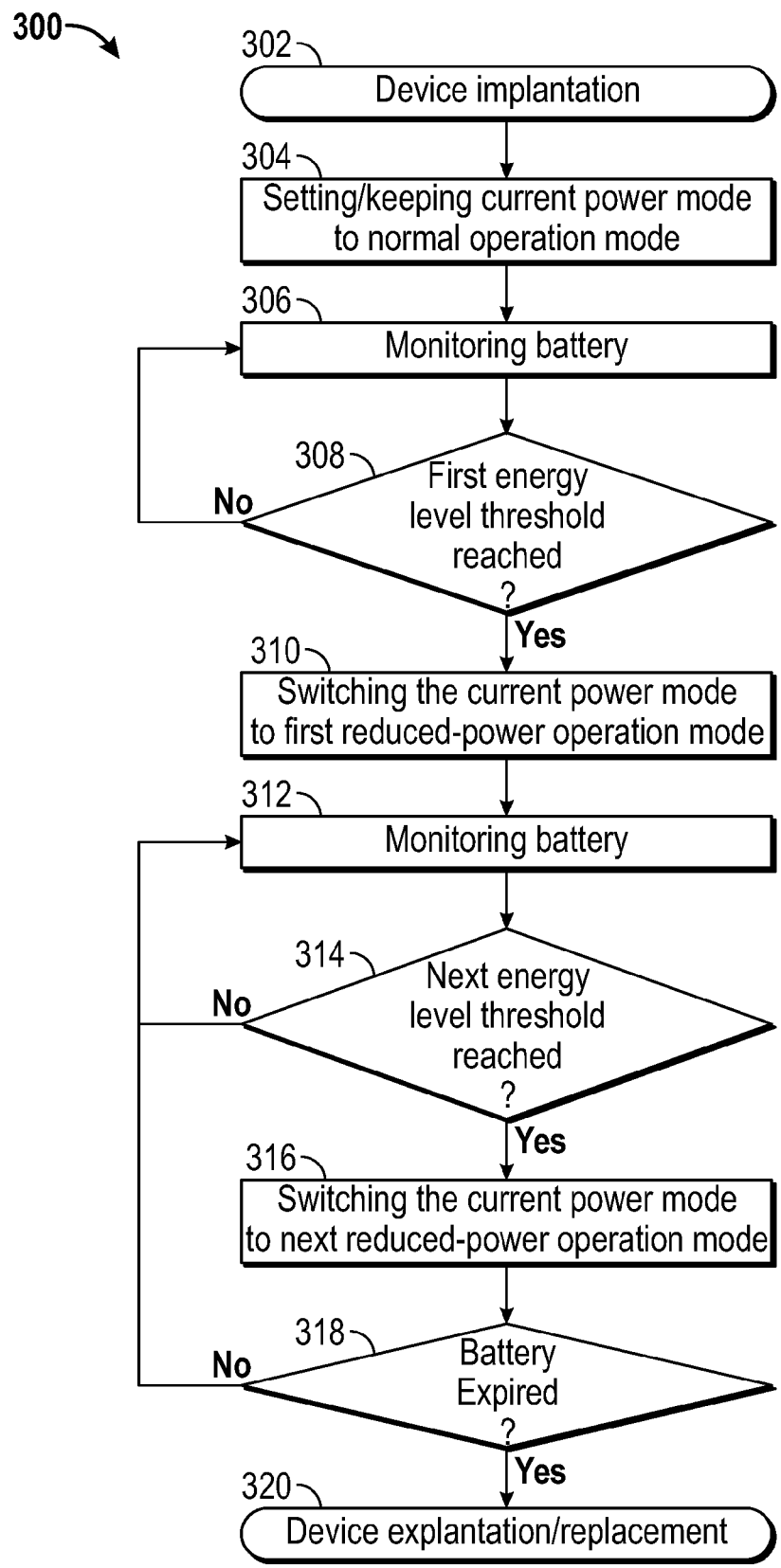
FIG. 3 is a flow chart illustrating an embodiment of a method for operating the IMD based on its battery status.

FIG. 3 is a flow chart illustrating an embodiment of a method 300 for operating an IMD such as IMD 210 based on its battery status. In one embodiment, control circuit 222 is programmed to perform method 300. The IMD has a plurality of power modes including the normal operation mode and the one or more reduced-power operation modes. The IMD has one or more functional modules each performing a monitoring or therapeutic function and a control circuit. The control circuit adjusts operation of at least one functional module of the one or more functional modules to reduce the overall power consumption of the IMD during each of the one or more reduced-power operation modes. In one embodiment, the overall power consumption is reduced in a tiered manner within a reduced-power operation mode.

At 302, the IMD is implanted into the patient. At 304, upon the implantation of the device, the current power mode of the IMD is set to the normal operation mode (or kept at the normal operation mode if such a mode is preset before the implantation). At 306, the battery of the IMD is monitored to produce the battery status parameter. If the battery status parameter indicates that the energy level has fallen below a first energy level threshold at 308, the current power mode is switched to the first reduced-power operation mode at 310. At 312, the battery is continued to be monitored during the first reduced-power operation mode. If the battery status parameter indicates that the energy level has fallen below the next energy level threshold at 314, the current power mode is switched to the next reduced-power operation mode at 316. If the next energy level threshold indicates that the battery has expired (i.e., about totally depleted) at 318, the IMD needs to be immediately explanted and replaced at 320, if determined necessary for the patient. Otherwise, steps 312, 314, 316, and 318 are repeated until the battery has expired.

Figure 4:
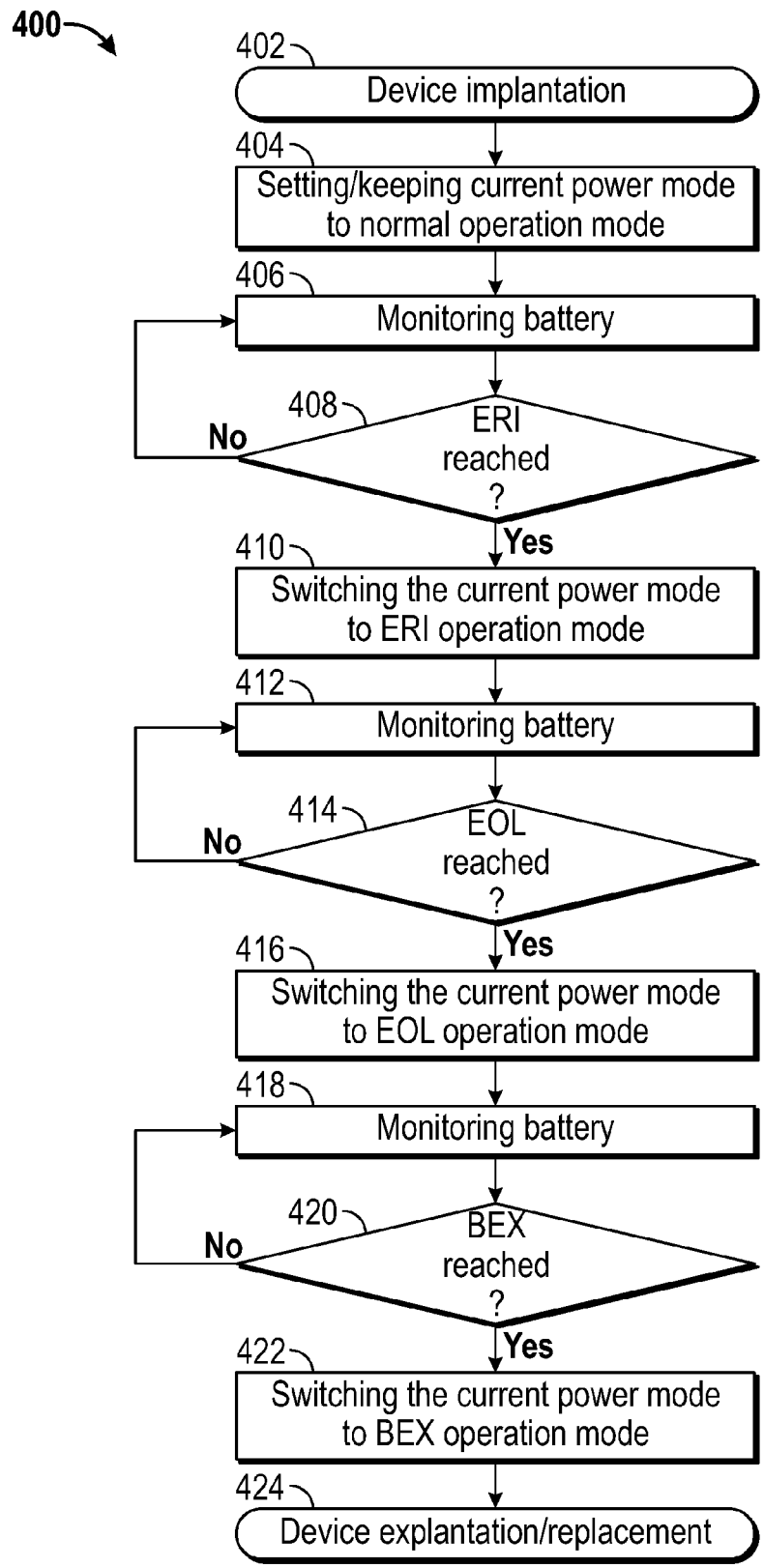
FIG. 4 is a flow chart illustrating an example of the method of FIG. 3 performed with a specific example of battery status parameter values.

FIG. 4 is a flow chart illustrating a method 400 being an example of method 300. In one embodiment, control circuit 222 and battery monitoring circuit 226 are programmed to perform method 400.

At 402, the IMD is implanted into the patient. At 404, upon the implantation of the device, the current power mode of the IMD is set to (or kept at) the normal operation mode. At 406, the battery of the IMD is monitored to produce the battery status parameter. If the battery status parameter indicates that ERI has been reached at 408, the current power mode is switched to the ERI operation mode at 410. At 412, the battery is continued to be monitored to produce the battery status parameter during the ERI operation mode. If the battery status parameter indicates that EOL has been reached at 414, the current power mode is switched to the EOL mode at 416. At 418, the battery is continued to be monitored to produce the battery status parameter during the EOL operation mode. If the battery status parameter indicates that BEX has been reached at 420, the current power mode is switched to the BEX mode at 422. During the BEX mode, the IMD is to be immediately explanted and replaced at 424, if determined to be necessary for the patient.

Figure 5:
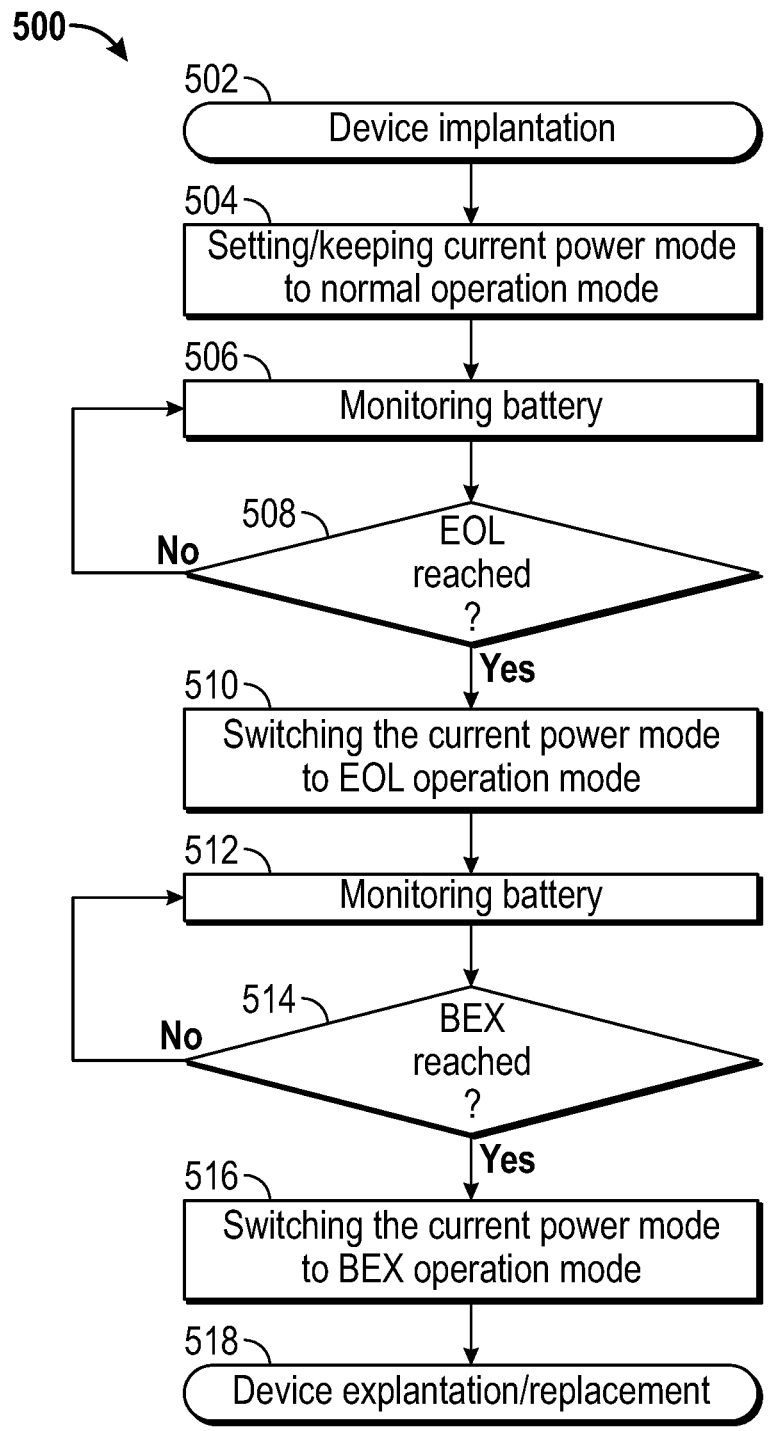
FIG. 5 is a flow chart illustrating another example of the method of FIG. 3 performed with another specific example of battery status parameter values.

FIG. 5 is a flow chart illustrating a method 500 being another example of method 300. In one embodiment, control circuit 222 and battery monitoring circuit 226 are programmed to perform method 500.

At 502, the IMD is implanted into the patient. At 504, upon the implantation of the device, the current power mode of the IMD is set to the normal operation mode. At 506, the battery of the IMD is monitored to produce the battery status parameter. If the battery status parameter indicates that EOL has been reached at 508, the current power mode is switched to the EOL operation mode at 510. At 512, the battery is continued to be monitored to produce the battery status parameter during the EOL operation mode. If the battery status parameter indicates that BEX has been reached at 514, the current power mode is switched to the BEX mode at 516. During the BEX mode, the IMD is to be immediately explanted and replaced at 518, if determined to be necessary for the patient.

Figure 6:
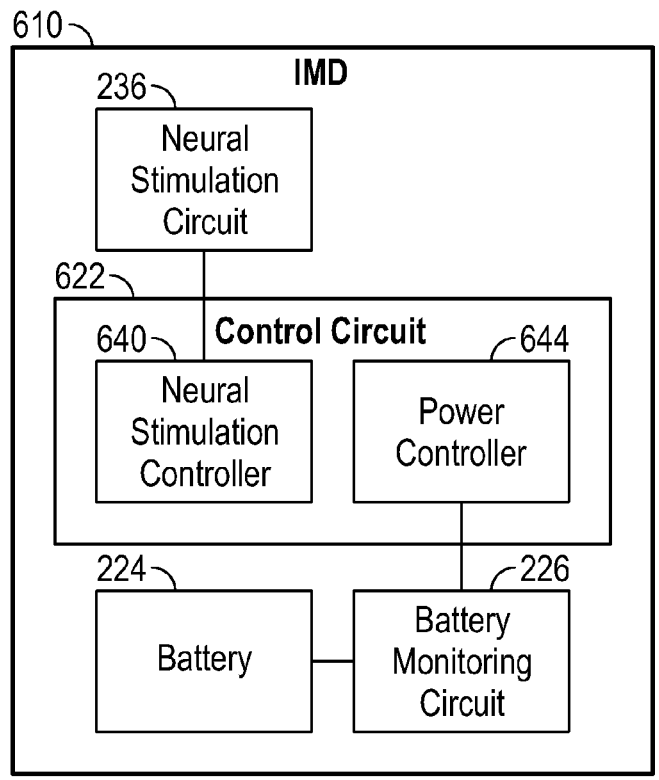
FIG. 6 is a block diagram illustrating an embodiment of an IMD that delivers neural stimulation and controls the delivery of the neural stimulation based on its battery status.

FIG. 6 is a block diagram illustrating an embodiment of an IMD 610 that delivers neural stimulation and controls the delivery of the neural stimulation based on its battery status. IMD 610 represents an embodiment of IMD 210 and is a stand-alone neural stimulator (i.e., without circuitry for cardiac stimulation). IMD 610 includes battery 224, battery monitory circuit 226, neural stimulation circuit 236, and a control circuit 622. Battery monitoring circuit 226 monitors the energy level of battery 224 and produces the battery status parameter indicative of the energy level. Neural stimulation circuit 236 delivers the neural stimulation to the nervous system of the patient. Control circuit 622 represents an embodiment of control circuit 222 and includes a power controller 644 and a neural stimulation controller 640. Power controller 644 sets the current power mode of IMD 610 to a reduced-power operation mode of a plurality of power modes of IMD 610 in response to the battery status parameter indicating that the energy level has fallen below an energy level threshold of a plurality of energy level thresholds. Neural stimulation controller 640 controls the delivery of the neural stimulation using neural stimulation parameters and adjusts one or more parameters of the neural stimulation parameters within the reduced-power operation mode such that, for example, an intensity of the neural stimulation is reduced in a tiered manner within the reduced-power operation mode according to a specified power reduction schedule.

Figure 7:
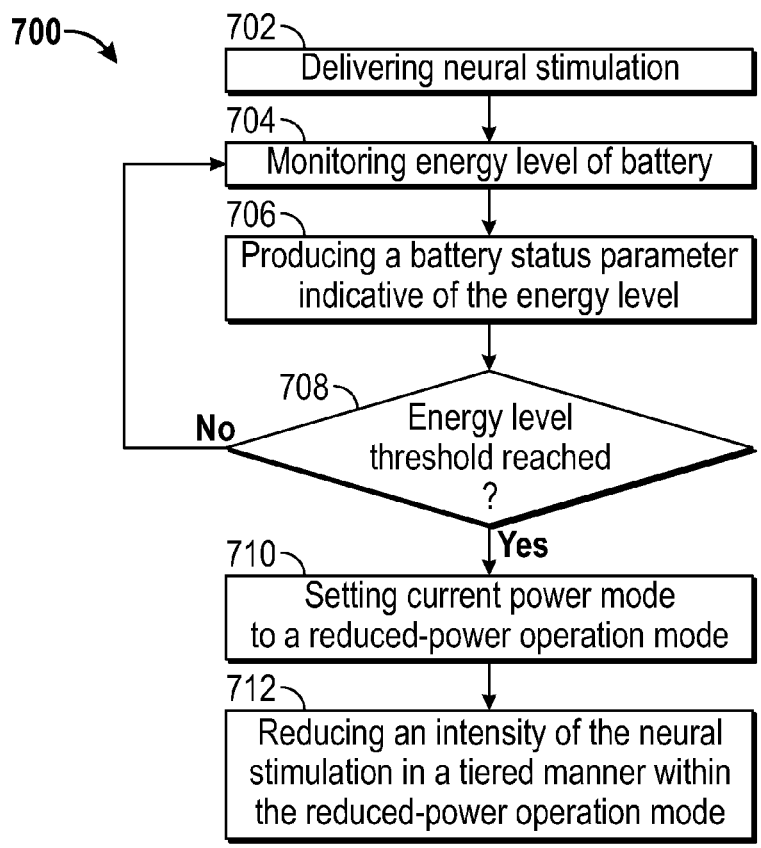
FIG. 7 is a flow chart illustrating an embodiment of a method for operating the IMD of FIG. 6.

FIG. 7 is a flow chart illustrating an embodiment of a method 700 for operating an IMD such as IMD 610. At 702, neural stimulation is delivered from the IMD. At 704, energy level of the battery of the IMD is monitored. At 706, a battery status parameter indicative of the energy level is produced. In response to the battery status parameter indicating that the energy level has fallen below an energy level threshold of a plurality of energy level thresholds at 708, the current power mode of the IMD is set to a reduced-power operation mode of a plurality of power modes of the IMD at 710. At 712, intensity of the neural stimulation is reduced in a tiered manner within the reduced-power operation mode by adjusting one or more parameters of the neural stimulation parameters according to a specified power reduction schedule.

Figure 8:
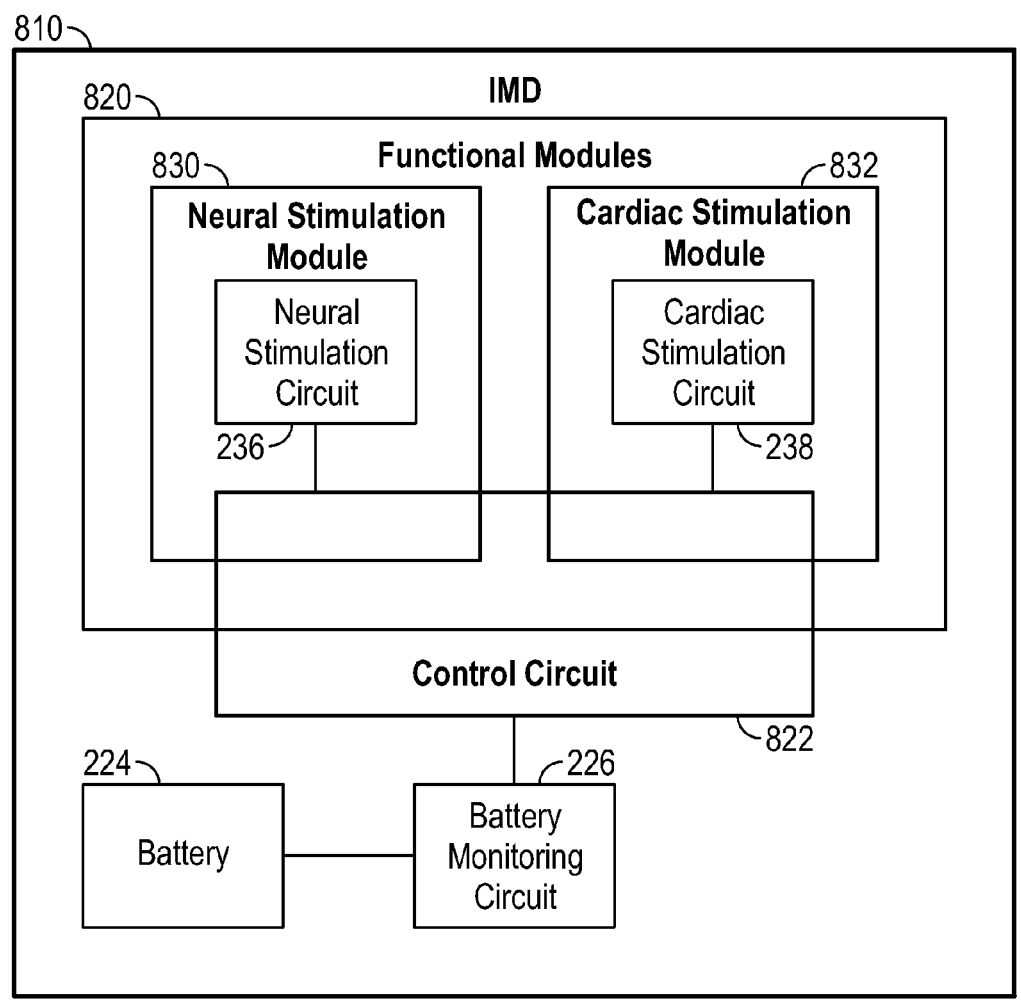
FIG. 8 is a block diagram illustrating an embodiment of an IMD that delivers neural stimulation and cardiac stimulation and controls the delivery of the neural stimulation and the delivery of the cardiac stimulation based on its battery status.

FIG. 8 is a block diagram illustrating an embodiment of an IMD 810 that delivers neural stimulation and cardiac stimulation and controls the delivery of the neural stimulation and the delivery of the cardiac stimulation based on its battery status. IMD 810 represents another embodiment of IMD 210 and is a combined neural and cardiac stimulation device. IMD 810 includes battery 224, battery monitoring circuit 226, a plurality of functional modules 820, and a control circuit 822. Battery monitoring circuit 226 monitors the energy level of battery 224 and produces a battery status parameter indicative of the energy level. Functional modules 820 include a neural stimulation module 830 and a cardiac stimulation module 832. Neural stimulation module 830 represents an embodiment of neural stimulation module 230 and includes neural stimulation circuit 236 that delivers the neural stimulation to the nervous system of the patient. Cardiac stimulation module 832 represents an embodiment of cardiac stimulation module 232 and includes cardiac stimulation circuit 238 that deliver the cardiac stimulation to the heart of the patient. Control circuit 822 represents an embodiment of control circuit 222 and controls operation of each functional module of functional module 820. In response to the battery status parameter indicating that the energy level has fallen below an energy level threshold of a plurality of energy level thresholds, control circuit 822 reduces intensity of the neural stimulation while maintaining intensity of the cardiac stimulation.

Figure 9:
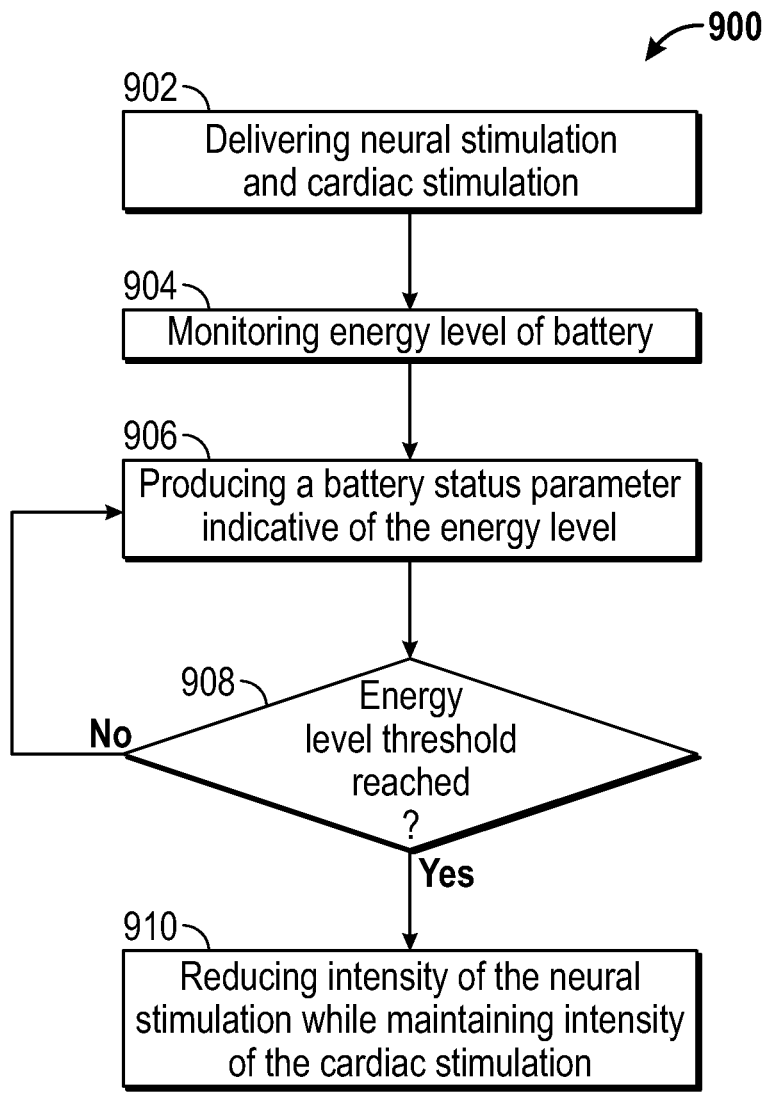
FIG. 9 is a flow chart illustrating an embodiment of a method for operating the IMD of FIG. 8.

FIG. 9 is a flow chart illustrating an embodiment of a method 900 for operating an IMD such as IMD 810. At 902, neural stimulation and cardiac stimulation are delivered from the IMD. At 904, the energy level of the battery of the IMD is monitored. At 906, a battery status parameter indicative of the energy level is produced. In response to the battery status parameter indicating that the energy level has fallen below an energy level threshold of a plurality of energy level thresholds at 908, intensity of the neural stimulation is reduced while intensity of the cardiac stimulation is maintained at 910.

Figure 10:
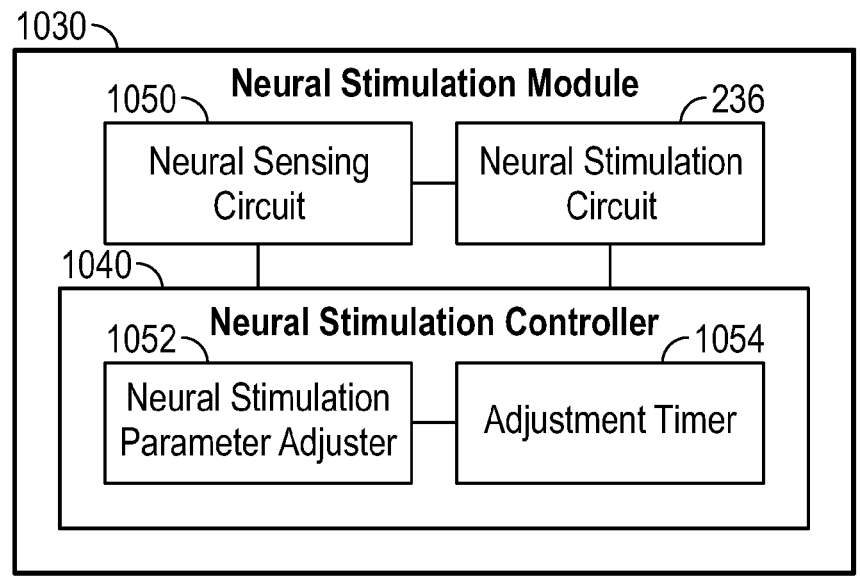
FIG. 10 is a block diagram illustrating an embodiment of a neural stimulation module of an IMD.

FIG. 10 is a block diagram illustrating an embodiment of a neural stimulation module 1030, which represents an embodiment of neural stimulation module 230. In the illustrated embodiment, neural stimulation module 1030 includes a neural sensing circuit 1050, neural stimulation circuit 236, and a neural stimulation controller 1040. Neural sensing circuit 1050 senses one or more neural signals for monitoring the patient's conditions and/or controlling the delivery of the neural stimulation. In various other embodiments, neural stimulation module 1030 may not include neural sensing circuit 1050. Neural stimulation circuit 236 delivers the neural stimulation to the nervous system of the patient. In one embodiment, the neural stimulation includes electrical pulses. In one embodiment, the neural stimulation is a non-life-sustaining therapy that is applied to enhance the patient's quality of life.

Neural stimulation controller 1040 represents an embodiment of neural stimulation controller 640 and may be part of a control circuit such as control circuit 222, 622, or 822, which is part of an IMD such as IMD 210, 610, and 810, respectively. The IMD has power modes each specifying a power state of neural stimulation module 1030. The control circuit includes a power controller that switches the current power mode of the IMD to the next power mode to reduce a power consumption required for delivering the neural stimulation. Neural stimulation controller 1040 controls the delivery of the neural stimulation by executing a neural stimulation algorithm for modulating electrical activities of the nervous system using the neural stimulation parameters according to the current power mode.

Neural stimulation controller 1040 includes a neural stimulation parameter 1052 and an adjustment timer 1054. Neural stimulation parameter adjuster 1052 adjusts one or more parameters of the neural stimulation parameters according to the current power mode. Adjustment timer 1054 controls timing of adjustment of the neural stimulation parameters within the current power mode such that an intensity of the neural stimulation (and hence a power consumption of neural stimulation module 1030) is reduced in a tiered manner within the current power mode according to a specified power reduction schedule. The power reduction schedule specifies a plurality of time intervals and one or more parameters of the neural stimulation parameters to be adjusted upon expiration of each time interval of the plurality of time intervals, such that the power consumption of the neural stimulation module is reduced upon expiration of each time interval of the plurality of time intervals. In other words, adjustment timer 1054 times a plurality of time intervals, and neural stimulation parameter adjuster 1052 adjusts one or more parameters of the neural stimulation parameters upon expiration of each time interval of the plurality of time intervals. The time intervals and the one or more parameters to be adjusted upon expiration of each time interval are predetermined by balancing the amount of reduction in the power consumption of neural stimulation module 1030 (and hence the IMD) and reduction of therapeutic effects of the neural stimulation.

In an example, the neural stimulation algorithm is an AMT algorithm including stimulation parameters selected to modulate one or more cardiovascular functions by delivering electrical pulses to one or more target nerves. Examples of the stimulation parameters include pulse amplitude, pulse width, pulse frequency (or inter-pulse interval), periodic dose, and duty cycle. The pulse amplitude and pulse width are selected to ensure that each pulse elicits an action potential in the target nerve. The periodic dose is a time interval during which a patient is treated with neural stimulation for each predetermined period. In one embodiment, the predetermined period is a day, and the periodic dose is a daily dose. The duty cycle is the duty cycle of the neural stimulation during the time interval of the period dose. For example, if the patient is to receive a neural stimulation therapy for two hours each day, the periodic dose is 2 hours/day (or the daily dose is 2 hours). If the neural stimulation during those two hours is delivered intermittently with alternating on- and off-periods, the duty cycle is the ratio of the on-period to the sum of the on-period and the off-period.

Examples of the stimulation parameters when the power state of the neural stimulation module is switched from the normal state to a reduced-power state, or from a reduced-power state to the next reduced-power state includes:
  pulse amplitude:
    reduced to a level exceeding a laryngeal vibration threshold by a specified margin, where laryngeal vibration is used to indicate neural capture, and the laryngeal vibration threshold is used as a neural capture threshold;
    reduced by a specified value (e.g., 1 mA) or specified percentage (e.g., 50%)
    reduced by a specified value or percentage but subject to a minimum level exceeding the laryngeal vibration threshold by the specified margin;
  pulse width;
    reduced by a specified amount (e.g., 300 to 200, or 150, or 120 µs);
  duty cycle:
    reduced by a specified percentage (e.g., about 50%, or 17% to 8%);
  periodic dose:
    reduced such as daily dose specified by the time interval during which the neural stimulation is delivered (e.g., reduced from continuous delivery to periodic delivery, or daily dose reduced from 24 hours to 12 or 8 hours);
  pulse frequency:
    reduced by a specified percentage (e.g., 25%:20 to 15 Hz; 50%:20 to 10 Hz).

In an example, the power reduction schedule specifies that the duty cycle is reduced upon switching to the next power mode (ERI or EOL mode), the periodic dose is reduced upon expiration of the first time interval of the plurality of time intervals, and the pulse amplitude is reduced upon expiration of the second time interval of the plurality of time intervals.

Figure 11:
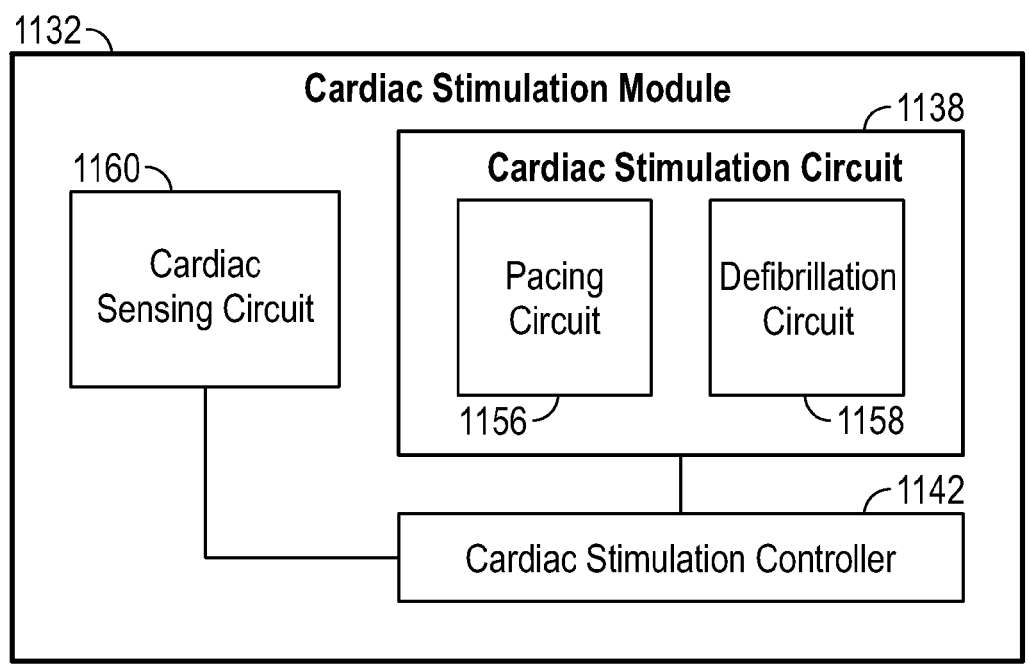
FIG. 11 is a block diagram illustrating an embodiment of a cardiac stimulation module of an IMD.

FIG. 11 is a block diagram illustrating an embodiment of a cardiac stimulation module 1132, which represents an embodiment of cardiac stimulation module 232. In the illustrated embodiment, cardiac stimulation module 1132 includes a cardiac sensing circuit 1160, a cardiac stimulation circuit 1138, and a cardiac stimulation controller 1142. Cardiac sensing circuit 1160 senses one or more cardiac signals for monitoring the patient's conditions and/or controlling the delivery of the cardiac stimulation. In various other embodiments, the one or more cardiac signals may also be used to control the delivery of the neural stimulation. Cardiac stimulation circuit 1138 represents an embodiment of cardiac stimulation circuit 238 and delivers cardiac stimulation to the heart of the patient. In the illustrated embodiment, cardiac stimulation circuit 1138 includes a pacing circuit 1156 and a defibrillation circuit 1158. Pacing circuit 1156 delivers pacing pulses to the heart. Defibrillation circuit 1158 delivers defibrillation pulses to the heart. In various embodiments, the cardiac stimulation is a life-sustaining therapy. For example, pacing circuit 1156 may deliver anti-bradycardia pacing pulses to the heart of a pacemaker-dependent patient, and defibrillation circuit 1158 delivers ventricular defibrillation pulses to the heart if the patient suffers from ventricular fibrillations.

Cardiac stimulation controller 1142 represents an embodiment of cardiac stimulation controller 242 and may be part of a control circuit such as control circuit 222 or 822, which is part of an IMD such as IMD 210 and 810, respectively. The IMD has power modes each specifying a power state of cardiac stimulation module 1132 in addition to the power state of neural stimulation module 1030. The control circuit includes a power controller that adjusts the power state of neural stimulation module 1030 to reduce its power consumption without adjusting the power state of cardiac stimulation module 1132 in response to the current power mode being switched to the next power mode. Cardiac stimulation controller 1142 controls the delivery of the cardiac stimulation by executing a cardiac stimulation algorithm for modulating electrical activities of the heart using cardiac stimulation parameters according to the current power mode. In various embodiments, cardiac stimulation controller 1142 adjusts one or more parameters to reduce intensity of the cardiac stimulation only when the cardiac stimulation includes at least one non-life-sustaining therapy. When the cardiac stimulation is considered life-sustaining, the available intensity of the cardiac stimulation is maintained in the reduced-power operation modes until the battery is unable to supply for such intensity.

In one embodiment, sensor module(s) 234 as illustrated in FIG. 2 include an activity sensor, such as an accelerometer, that senses an activity signal indicative of a physical activity level. Cardiac stimulation controller 1142 may use the sensed activity level to control the delivery of pacing pulses. In various embodiments, sensor module(s) 234 as illustrated in FIG. 2 may include any sensors used for monitoring of the patient, control of the neural stimulation by neural stimulation controller 1040, and/or control of cardiac stimulation by cardiac stimulation controller 1142. Examples of such sensors include the activity sensor, a sensor for leadless sensing of cardiac activities, an impedance sensor for sensing cervical impedance plethysmogram, and/or a respiratory sensor for sensing tidal volume and/or minute ventilation.

In various embodiments, IMD 210 includes neural stimulation module 230 and sensor module(s) 234. The power modes of IMD 210 each specify a power state of each sensor of sensor module(s) 234, in addition to the power state of neural stimulation module 230. In various other embodiments, IMD 210 includes neural stimulation module 230, cardiac stimulation module 232, and sensor module(s) 234. The power modes of IMD 210 each specify a power state of each sensor of sensor module(s) 234, in addition to the power state of neural stimulation module 230 and the power state of cardiac stimulation module 232. In one embodiment, power controller 244 disables at least one sensor module of sensor module(s) 234 in response to the current power mode being switched to the next power mode. In one embodiment, power controller 244 adjusts the power state of neural stimulation module 230 to reduce its power consumption and adjusts the power state of at least one sensor module of sensor module(s) 234 to reduce the power consumption of sensor module(s) 234 without adjusting the power state of cardiac stimulation module 232 in response to the current power mode being switched to the next power mode. For example, power controller 244 may set the power state of cardiac stimulation module 232 to the normal state, set the power state of neural stimulation module 230 to the reduced-power state or the low-power state, and set the power state of at least one sensor module of sensor module(s) 234 to the reduced-power state or the low-power state during a reduced-power mode in response to the current power mode being switched to the next power mode.

In response to the current power mode being switched to the next power mode, at least one sensor module of sensor module(s) 234 may be disabled, and consequently control of the neural stimulation and/or cardiac stimulation may change from closed-loop to open-loop. If the disabled sensor module includes a sensor used by neural stimulation controller 1040 to control the delivery of the neural stimulation, and the neural stimulation continues to be delivered, neural stimulation controller 1040 switches the control of the delivery from closed-loop (using the sensor) to open-loop. If the disabled sensor module includes a sensor used by cardiac stimulation controller 1142 to control the delivery of the cardiac stimulation, and the cardiac stimulation continues to be delivered, cardiac stimulation controller 1142 switches the control of the delivery from closed-loop (using the sensor) to open-loop.

In one embodiment, when the current power mode of IMD 210 is in one of the one or more reduced-power operation modes, telemetry circuit 228 is set to a reduced-power state in which inductive telemetry is supported while far-field radio-frequency telemetry is disabled. In another embodiment, neural stimulation module 230 and/or cardiac stimulation module 232 are each set to the reduced-power state or low-power state during a telemetry session, i.e., when telemetry circuit 228 is transmitting and/or receiving signals. In various embodiments, the longevity of IMD 210 can be increased by suspending or reducing intensity of one or more non-life-sustaining therapies during a telemetry session. In one embodiment, the one or more non-life-sustaining therapies are suspended or adjusted for reduced intensity when the current power mode of IMD 210 is in one of the one or more reduced-power operation modes. In one embodiment, the one or more non-life-sustaining therapies are suspended or adjusted for reduced intensity during a far-field radio-frequency telemetry session i.e., when telemetry circuit 228 is transmitting and/or receiving signals via far-field radio-frequency telemetry. In one embodiment, the one or more non-life-sustaining therapies include one or more neural stimulation therapies. When neural stimulation module 230 is set to the reduced-power or low-power state, battery 224 can be run to a lower charge state while still providing IMD 210 the ability to communicate with external system 114 via telemetry.

In various embodiments, when the current power mode of IMD 210 is set to one of the one or more reduced-power operation modes, sensed cardiac and other physiological signals may no longer be stored in IMD 210. In various embodiments, when the current power mode of IMD 210 is set to one of the one more reduced-power operation modes, daily wake-up sessions of IMD 210 and/or communication sessions of IMD 210 with external system 114 may be reduced or suspended. In general, any portion of IMD 210 that can be safely set to a reduced-power state may be set to the reduced-power state when the need for conserving battery energy arises, as determined by those skilled in the art.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device for use in a body, comprising:
    a battery;
    a battery monitoring circuit coupled to the battery, the battery monitoring circuit configured to monitor an energy level of the battery and produce a battery status parameter indicative of the energy level;
    a neural stimulation circuit configured to deliver neural stimulation for modulating neural activities; and
    a control circuit coupled to the battery monitoring circuit and the neural stimulation circuit, the control circuit including:
        a power controller configured to set a current power mode of the implantable medical device to a first reduced-power operation mode of a plurality of power modes in response to the battery status parameter indicating that the energy level has fallen below a first energy level threshold of a plurality of energy level thresholds; and
        a neural stimulation controller configured to control the delivery of the neural stimulation using neural stimulation parameters and to adjust one or more parameters of the neural stimulation parameters within the first reduced-power operation mode according to a power reduction schedule, wherein the power reduction schedule specifies a plurality of predetermined time intervals, and the neural stimulation controller is configured to adjust the one or more parameters upon expiration of each time interval of the plurality of predetermined time intervals such that the intensity of the neural stimulation is reduced in a tiered manner within the first reduced-power operation mode.

2. The implantable medical device of claim 1, wherein the battery monitoring circuit is configured to measure one or more battery parameters indicative of an energy level of the battery and generate values of the battery status parameter each indicating whether the energy level of the battery has fallen below one energy level threshold of a plurality of energy level thresholds.

3. The implantable medical device of claim 2, wherein the power controller is configured to set the current power mode to a normal operation mode of the plurality of power modes before the battery status parameter indicates that the energy level has fallen below the first energy level threshold and switch the current power mode from the normal operation mode to the first reduced-power operation mode in response to the battery status parameter indicating that the energy level has fallen below the first energy level threshold.

4. The implantable medical device of claim 3, wherein the power controller is configured to switch the current power mode from the first reduced-power operation mode to the next reduced-power operation mode during which the intensity of the neural stimulation is further reduced in response to the battery status parameter indicating that the energy level has fallen below a next energy level threshold of the plurality of energy level thresholds.

5. The implantable medical device of claim 1, wherein the neural stimulation circuit is configured to deliver electrical pulses, and the neural stimulation parameter adjuster is configured to adjust at least a duty cycle during the first reduced-power operation mode.

6. The implantable medical device of claim 5, wherein the neural stimulation parameter adjuster is configured to adjust at least a periodic dose and the duty cycle during the first reduced-power operation mode.

7. The implantable medical device of claim 6, wherein the neural stimulation parameter adjuster is configured to adjust at least a pulse amplitude, the periodic dose, and the duty cycle during the first reduced-power operation mode.

8. The implantable medical device of claim 1, further comprising a cardiac stimulation circuit to deliver cardiac stimulation including one or more of cardiac pacing or defibrillation, and wherein the control circuit is configured to reduce the intensity of the neural stimulation without reducing an intensity of the cardiac stimulation during the first reduced-power operation mode.

9. The implantable medical device of claim 5, further comprising a telemetry circuit coupled to the control circuit and configured to transmit and receive signals, and wherein the neural stimulation controller is configured to control the delivery of the neural stimulation under the first reduced-power operation mode such that the intensity of the neural stimulation is reduced during a telemetry session during which the telemetry circuit transmits and receives signals.

10. A method for operating an implantable medical device in a body, comprising:
    monitoring an energy level of a battery of the implantable medical device;
    producing a battery status parameter indicative of the energy level;
    delivering neural stimulation for modulating neural activities;
    controlling the delivery of the neural stimulation using neural stimulation parameters;
    setting a current power mode of the implantable medical device to a first reduced-power operation mode of a plurality of power modes in response to the battery status parameter indicating that the energy level has fallen below a first energy level threshold of a plurality of energy level thresholds; and
    reducing an intensity of the neural stimulation in a tiered manner within the first reduced-power operation mode by adjusting one or more parameters of the neural stimulation parameters according to a specified power reduction schedule, including:
        timing a plurality of predetermined time intervals specified in the power reduction schedule; and
        adjusting the one or more parameters upon expiration of each time interval of the plurality of predetermined time intervals to reduce the intensity of the neural stimulation upon the expiration of the each time interval.

11. The method of claim 10, wherein monitoring the energy level comprises:
   measuring one or more battery parameters indicative of an energy level of the battery; and
   generating values of the battery status parameter, the values each indicating whether the energy level of the battery has fallen below one energy level threshold of a plurality of energy level thresholds.

12. The method of claim 11, wherein measuring the one or more battery parameters indicative of the energy level comprises measuring a terminal voltage being a voltage across two terminals of the battery.

13. The method of claim 11, wherein measuring the one or more battery parameters comprises measuring a charge depletion parameter indicative of a cumulative charge depleted from the battery.

14. The method of claim 11, comprising setting the current power mode to a normal operation mode of the plurality of power modes before the battery status parameter indicates that the energy level has fallen below the first energy level threshold.

15. The method of claim 14, comprising:
   switching the current power mode from the first reduced-power operation mode to a next reduced-power operation mode of the plurality of power modes in response to the battery status parameter indicating that the energy level has fallen below a next energy level threshold of the plurality of energy level thresholds; and
   reducing the intensity of the neural stimulation according to the next reduced-power operation mode.

16. The method of claim 14, wherein delivering the neural stimulation comprises delivering electrical pulses, and adjusting the one or more parameters of the neural stimulation parameters according to the specified power reduction schedule comprises adjusting one or more of a duty cycle, a periodic dose, a pulse amplitude, a pulse width, or a pulse frequency within the first reduced-power operation mode.

17. The method of claim 10, further comprising delivering cardiac stimulation including one or more of cardiac pacing or defibrillation, and reducing the intensity of the neural stimulation without reducing an intensity of the cardiac stimulation during the first reduced-power operation mode.

18. The method of claim 17, wherein delivering the neural stimulation comprising executing an autonomic modulation therapy algorithm for modulating autonomic nervous activities.

19. The implantable medical device of claim 1, wherein the neural stimulation controller is configured to control the delivery of the neural stimulation by executing an autonomic modulation therapy algorithm for modulating autonomic nervous activities using neural stimulation parameters selected to modulate one or more cardiovascular functions.

20. The method of claim 16, wherein adjusting the one or more parameters comprises reducing the pulse amplitude to a level exceeding a laryngeal vibration threshold by a specified margin, wherein laryngeal vibration is used to indicate neural capture, and the laryngeal vibration threshold is used as a neural capture threshold.

* * * * *